(12) United States Patent
Rissing et al.

(10) Patent No.: US 10,247,665 B2
(45) Date of Patent: Apr. 2, 2019

(54) DEVICE FOR DETERMINING A CONCENTRATION OF A CHEMICAL SUBSTANCE

(71) Applicant: GOTTFRIED WILHELM LEIBNIZ UNIVERSITÄT HANNOVER, Hannover (DE)

(72) Inventors: Lutz Rissing, Munich (DE); Stephanie Holz, Springe/Altenhagen (DE); Dominik Hoheisel, Hannover (DE)

(73) Assignee: Gottfried Wilhelm Leibniz Universitaet Hannover, Hannover (DE)

( * ) Notice: Subject to any disclaimer, the term of this patent is extended or adjusted under 35 U.S.C. 154(b) by 0 days.

(21) Appl. No.: 15/111,341

(22) PCT Filed: Jan. 19, 2015

(86) PCT No.: PCT/EP2015/000076
§ 371 (c)(1),
(2) Date: Jul. 13, 2016

(87) PCT Pub. No.: WO2015/106969
PCT Pub. Date: Jul. 23, 2015

(65) Prior Publication Data
US 2016/0334328 A1  Nov. 17, 2016

(30) Foreign Application Priority Data
Jan. 17, 2014 (DE) .................. 10 2014 000 651

(51) Int. Cl.
G01N 21/31 (2006.01)
G01N 21/03 (2006.01)
G01N 21/05 (2006.01)

(52) U.S. Cl.
CPC ....... G01N 21/3151 (2013.01); G01N 21/031 (2013.01); G01N 21/05 (2013.01); *G01N 2201/06113* (2013.01)

(58) Field of Classification Search
CPC ........ G01N 21/31; G01N 21/03; G01N 21/05; G01N 21/3151; G01N 2201/06113
(Continued)

(56) References Cited

U.S. PATENT DOCUMENTS 4,507,558 A * 3/1985 Bonne ................ G01N 21/3504
                                                    250/338.1
5,222,389 A * 6/1993 Wong .................... G01N 1/2258
                                                    250/338.5
(Continued)

FOREIGN PATENT DOCUMENTS

DE    10023000 A1    1/2002
DE    10031560 A1    10/2002
(Continued)

OTHER PUBLICATIONS

Bomse, D., "Final Report: A Compact, Low-Cost, Near-UV Sensor for Chlorine Dioxide", Reasearch Project Database, Jun. 4, 2007, Web.

*Primary Examiner* — Isiaka O Akanbi
(74) *Attorney, Agent, or Firm* — W & C IP

(57) ABSTRACT

The invention relates to a device tier determining a concentration of a chemical substance dissolved in a liquid, which chemical substance absorbs light (10) of an absorption wavelength, wherein the device comprises: at least one flow-through chamber (2) having at least one inlet opening (4), at least one outlet opening (6), and at least one peripheral wall (24); at least one laser (8) for emitting light (10) of the absorption wavelength; and at least one detector (18) for detecting the emitted light (10); wherein the laser (8) and the detector (18) are arranged in such a way that the light (10)
(Continued)

Figure 1:
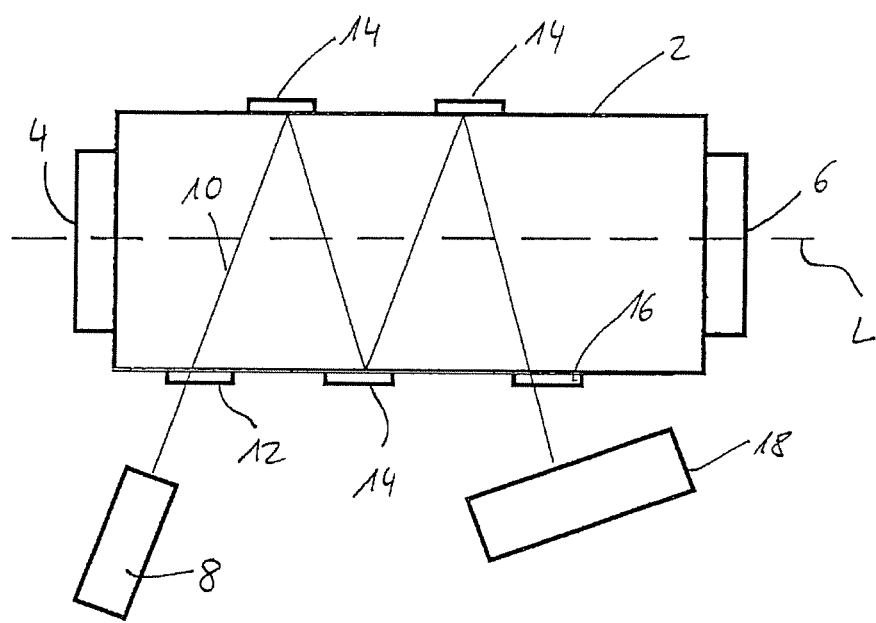

emitted by the laser (8) is conducted through the flow-through chamber (2) along at least two different paths before said light hits the detector (18), and wherein the device has two lasers (8) which emit light of different wavelengths. The invention further relates to a method for producing a flow-through chamber for such a device.

11 Claims, 4 Drawing Sheets

(58) Field of Classification Search
USPC .................................. 356/432–438, 73, 246
See application file for complete search history.

(56) References Cited

U.S. PATENT DOCUMENTS

| | | | |
|---|---|---|---|
| 5,485,276 A | 1/1996 | Bien et al. | |
| 6,388,752 B1* | 5/2002 | Ziegler | G01N 21/532 |
| | | | 356/342 |
| 6,661,011 B2* | 12/2003 | Chang | G01N 21/3504 |
| | | | 250/343 |
| 6,791,689 B1* | 9/2004 | Weckstrom | G01J 3/10 |
| | | | 356/437 |
| 7,502,114 B2* | 3/2009 | Levine | G01N 21/3151 |
| | | | 356/432 |
| 8,253,930 B2 | 8/2012 | Akiyama et al. | |
| 2003/0025909 A1* | 2/2003 | Hallstadius | A23L 3/003 |
| | | | 356/436 |
| 2005/0200848 A1 | 9/2005 | Levine et al. | |
| 2007/0215817 A1 | 9/2007 | Shirai et al. | |
| 2010/0238446 A1* | 9/2010 | Akiyama | G01N 21/031 |
| | | | 356/437 |
| 2011/0216322 A1* | 9/2011 | Moriya | G01N 15/0205 |
| | | | 356/433 |

FOREIGN PATENT DOCUMENTS

| | | |
|---|---|---|
| DE | 10322894 A1 | 12/2004 |
| DE | 602004011063 T2 | 1/2009 |
| DE | 202010007065 U1 | 11/2010 |
| DE | 102009025147 B3 | 12/2010 |
| DE | 102010050626 A1 | 8/2012 |
| EP | 1535047 B1 | 6/2009 |
| WO | 2006/132980 A2 | 12/2006 |
| WO | 2010/096074 A1 | 8/2010 |
| WO | 2013/119320 A1 | 8/2013 |

\* cited by examiner

DEVICE FOR DETERMINING A CONCENTRATION OF A CHEMICAL SUBSTANCE

The invention relates to a device for determining a concentration of a chemical substance dissolved in a liquid, which substance absorbs light of one absorption wavelength, the device comprising at least one flow-through chamber having at least one inlet opening, at least one outlet opening and at least one peripheral wall, at least one laser for emitting light of the absorption wavelength and at least one detector for detecting the emitted light, the laser and the detector being arranged such that the light emitted by the laser is conducted through the flow-through chamber along at least two different paths before it hits the detector. The invention moreover relates to a method for producing a flow-through chamber for such a device.

In many different technical fields of application, it is necessary and advantageous to know a concentration of a chemical substance dissolved in a liquid. In this connection, an especially important example is drinking water treatment, which involves removing harmful substances of an organic and inorganic nature from the drinking water. Different methods have been used to this end in the past.

Widely used in this connection are chemical methods, in which, for example, the addition of aqueous chlorine solutions kills harmful substances and pathogens as a result of the particular undesired constituents of the drinking water reacting with the chlorine atoms, producing new chlorine compounds. Although said compounds are not harmful to health in a low concentration, they lead to skin and mucosa irritations such as, for example, chlorine spots or watery eyes.

As an alternative to using aqueous chlorine solutions, chlorine dioxide was introduced as a pathogen-killing additive. This has the advantage that, owing to the chlorine dioxide, no chlorine compounds are formed with the undesired constituents of the water, but that, instead, the undesired constituents are destroyed by oxidation. As a result, the pH of the water is also virtually unaltered. A further advantage of the chlorine dioxide is that it is virtually odorless and tasteless in the typical drinking water usage concentrations. However, used in excessively large doses, it is harmful to health. Therefore, when using chlorine dioxide, the concentration of this substance in the water must be monitored, so that only concentrations not harmful to humans are present in the drinking water.

In order to measure chlorine dioxide concentrations, ion-selective electrodes or probes are proposed for example, as is the case for example in DE 60 2004 011 063 T2. Alternatively, use is also made of amperometric measurement cells, as described for example in DE 100 31 560 A1. DE 20 2010 007 065 U1 describes a chloride measurement system in which a combination of measurement branches and measurement cells which are immersed into an aqueous solution are used. A further amperometric and voltammetric sensor is described in DE 103 22 894 A1.

However, all these devices and methods have the disadvantage that they, on the one hand, require great expenditure in terms of apparatus and must be calibrated using an independent colorimetric method such as DPD determination. This is especially the case for the amperometric and voltammetric sensors. For the determination of the chlorine dioxide concentration in drinking water, these methods and sensors are therefore only of limited suitability, since the colorimetric measurement methods at, for example, relatively high temperatures are tainted with high errors owing to the increased vapor pressure of the chlorine dioxide and thus the loss thereof prior to detection and the described methods and sensors cannot therefore be calibrated reliably. Furthermore, it is not possible either to reliably carry out the measurement of concentrated chlorine dioxide solutions, reported in gram/liter.

WO 2010/096074 A1 describes a chlorine dioxide sensor which can detect gaseous chlorine dioxide. The gas mixture containing chlorine dioxide is conducted through a flow-through chamber and illuminated in said chamber by means of an LED emitting ultraviolet light. In this case, the LED emits light for 50 ms for example. Between two of these light pulses, there are approximately 5 seconds in which no light is emitted.

Chlorine dioxide absorbs light at an absorption wavelength of approximately 360 nm. The UV LED emits light of exactly said wavelength, and so, at the end of the flow-through chamber that is opposite to the LED, a detector is capable of measuring the intensity of the incoming light of said absorption wavelength. From the intensity loss, which is a measure of the degree of absorption of the light inside the flow-through chamber, it is possible to determine the concentration of the chlorine dioxide.

The very long interval between two consecutive impulses in the case of a sensor according to WO 2010/096074 A1 is due to the photoreactivity of the chlorine dioxide. Thus, it is described as advantageous that the device is used in a lightproof box in order to prevent the chlorine dioxide being exposed to too much scattered light. In this case, toxic and/or explosive substances might develop, and this must naturally be avoided.

The sensor described in the aforementioned publication is not suitable for the detection of chlorine dioxide in water, since the absorption cross section of the chlorine dioxide strongly decreases in water, and so it is no longer possible to detect, in particular, small concentrations, which are of interest especially in the testing of drinking water.

Moreover, a disadvantage in the case of the detector described in WO 2010/096074 A1 is that a relatively large detection area must be used in order to hit a sufficient amount of chlorine dioxide molecules with the incident UV light in order to attain a measurable lowering of the intensity. Therefore, the detectors described therein are very cost-intensive and space-consuming.

A range of generic devices are known from the prior art. For instance, U.S. Pat. No. 5,485,276 describes a method for monitoring a concentration of a chemical substance dissolved in a fluid. DE 10 2009 025 147 B3, DE 10 2010 050 626 B4 and EP 1 535 047 B1 describe gas spectrometers which all use laser light and are based on the measurement of the absorption of said light. WO 2006/132380 A2 and US 2007/0215817 A1 each describe methods and devices for detecting individual molecules, the US publication specializing especially in DNA molecules. U.S. Pat. No. 8,253,930 B2 discloses a device for determining the amount of moisture in a gas. However, all these devices are not suitable for qualitatively valuable measurements of the concentration of a chemical substance dissolved in a liquid.

It is therefore an object of the invention to propose a device for determining a concentration of a chemical substance which is dissolved in a liquid and which absorbs light of one absorption wavelength, which device can also securely and reliably detect small concentrations of the substance in the liquid and, moreover, can be designed to be structurally small. It is a further object of the invention to propose a method for producing a flow-through chamber for such a device.

The invention achieves the stated object by a device for determining a concentration of a chemical substance which is dissolved in a liquid and which absorbs light of one absorption wavelength, according to the preamble of claim 1, which device is notable for the fact that it comprises two lasers which emit light of differing wavelength.

The device according to the present invention also consequently makes use of the fact that the chemical substance to be detected absorbs light of one absorption wavelength. During operation of the device, the liquid in which the dissolved chemical substance is situated is conducted through the flow-through chamber. In this connection, the liquid is introduced into the flow-through chamber through the at least one inlet opening and leaves said chamber through the at least one outlet opening. By means of the laser, light of the absorption wavelength is introduced into the flow-through chamber, which passes said light along at least two different paths. Subsequently, the light hits the detector, which is geared to detecting the intensity of said light. From the known incidence intensity and the detected measurement intensity, it is possible to determine the level of the absorption of the light inside the flow-through chamber, which level is a direct measure of the concentration of the chemical substance, for example of the chlorine dioxide. In this connection, the device has preferably, though not necessarily, an electrical control system which is geared to determining the concentration of the chemical substance in the liquid from the measured values of the detector and the known incident light intensity due to the laser.

The device according to the invention is also suitable for detecting, for example, chlorine dioxide in water. Since detection is carried out by using a laser which transmits a distinctly greater light intensity into the flow-through chamber than is the case by the UV LED known from the prior art, the lower absorption cross section of the chlorine dioxide in the water is compensated for, and so a measurement signal having sufficient resolution is obtained.

Owing to the feature that the light passes through the flow-through chamber along at least two different paths, what is additionally achieved is that the path length of the light in the flow-through chamber can be selected larger than a spatial elongation of the flow-through chamber in one spatial direction. As a result, on its way through the flow-through chamber, the light hits more molecules of the chemical substance to be detected, distinctly increasing the sensitivity of detection of the device. The fact that it is, for example, even possible to detect chlorine dioxide in water in concentrations not harmful to human health is thus achieved. In this connection, detectable concentrations can definitely be within the range of "parts per billion" (ppb). Using the chlorine dioxide sensors known from the prior art, it has so far not been possible to securely and reliably detect such small concentrations in water.

It is known to determine concentrations of a chemical substance distributed in a gas by means of a device according to the preamble of claim 1. Although the use of such a generic device without the inventive feature for determining a concentration of a dissolved chemical substance in a liquid, for example water, leads to a measurement value, since a portion of the laser radiation is absorbed, it is not possible to reliably state the concentration of the chemical substance that is present in the liquid. The invention is based on the insight that a portion of the incident laser light of the absorption wavelength is absorbed, even though it does not hit the chemical substance to be detected. In contrast to a gas to be tested, a liquid contains contaminants, for example in the form of small bubbles or suspended particles, which likewise ensure an absorption or scattering of the incident laser light and thus falsify the measurement result. These effects are virtually independent of the wavelength of the incident light. The invention makes use of this by using a second laser which emits light of one wavelength which is advantageously not absorbed by the dissolved chemical substance, the concentration of which is to be determined. The light of the second laser is conducted through the flow-through chamber too. This light too is consequently scattered at the contaminants, and so the entire incident laser intensity of the second laser light emitted by the second laser is not detected at the detector. In this connection, it is ensured that the thus determined decrease in intensity of the second laser light transmitted by the second laser is not caused by the chemical substance to be detected. From both decreases in intensity of the light emitted by the two lasers at both wavelengths, it is thus possible to determine the influence of the scattering mechanisms and remove it by calculation from the decrease in intensity of the light of the absorption wavelength. It is thus possible to reliably state the concentration of the chemical substance to be detected, since it is ensured that wavelength-independent effects, such as scattering at contaminants for example, have been taken into account.

In one advantageous design of the device, the peripheral wall has at least one reflection segment which is arranged such that light emitted by the laser is deflected at the reflection semgent from a first path to a second path. In this connection, the reflection semgent can, for example, be a mirror which is attached to the peripheral wall and which is hit by the light of the absorption wavelength that is emitted by the laser. Said design having a single reflection segment has the advantage that laser and detector can be arranged on the same side of the peripheral wall of the flow-through chamber. This is naturally the case too with any other odd number of reflection semgents. Moreover, what is achieved by said design is that the light has to be conducted into the flow-through chamber at only one location and conducted out of the flow-through chamber at only one location, and can nevertheless pass through two different paths inside the flow-through chamber. If the light emitted by the laser is reflected only once inside the flow-through chamber, the path before the reflection forms the first path, whereas the light after the reflection passes through the second path.

In this connection, it has been found to be advantageous when the light from the laser is introduced into the flow-through chamber at, for example, one location of the peripheral wall and propagates in the flow-through chamber at an angle which is not equal to 0° and not equal to 90°, relative to a longitudinal extent of the flow-through chamber. Advantageously, this longitudinal extent runs in a direction which also corresponds to the flow-through direction in which the liquid containing the chemical substance to be detected flows from the inlet opening to the outlet opening of the flow-through chamber.

In this connection, the flow-through chamber itself can, for example, be designed to be in the shape of a hollow cylinder or in the shape of a hollow cuboid. Naturally, all other geometric designs of the flow-through chamber are also conceivable. The light emitted by the laser is advantageously reflected at least once at the peripheral wall at the reflection segment intended therefor and thus passes through the flow-through chamber along different paths.

In this connection, it has been found to be particularly advantageous when the light emitted by the laser is reflected multiple times by a reflection segment of the peripheral wall before it hits the detector. In this way, the distance covered by the light within the flow-through chamber can be adjusted virtually as desired and enlarged to the desired value. Said value can be adjusted especially according to the concentration that is to be expected and to be detected for the chemical substance. The lower the concentration that is expected and to be detected for the chemical substance, the longer the distance should be selected, which distance must be covered by the laser light inside the flow-through chamber before said light hits the detector. This ensures that, even in the case of small and most minute concentrations of the chemical substance, sufficient molecules are hit by the laser light to result in a measurable and detectable decrease in the intensity of the incident laser light. In this connection, virtually no limits are set in the actual selection of the path covered by the laser light inside the flow-through chamber. The subpaths can be in different planes or the same plane and, for example, intersect. Naturally, paths which do not intersect are also conceivable.

By selecting the intended reflections of the laser-emitted light inside the flow-through chamber, it is consequently possible to adjust the path length covered by the light inside the flow-through chamber virtually as desired. This means that there are thereby virtually no longer any restrictions on the size of the flow-through chamber. Said chamber can therefore be designed to be structurally small and have, for example, a length of a few millimeters, for example 4 mm. In the case of a flow-through chamber which is constructed in the shape of a cuboid and has, for example, dimensions of 4 mm×2 mm×2 mm, it is possible, with appropriate selection of the path which must be covered by the light inside the flow-through chamber, to detect even small and most minute concentrations of the chemical substance. This small design of the flow-through chamber leads to it being possible for the entire device to be designed to be structurally small and to be thus attached even at inaccessible or spatially limited locations, for example in or on a pipe system for drinking water.

In this connection, the device is, for example, attached in the form of a bypass to a pipe through which the liquid containing the chemical substance dissolved therein is conducted. In this way, a small portion of the liquid is then conducted through the flow-through chamber and exposed to the electromagnetic radiation of the laser. Assuming that there is a homogeneous distribution of the chemical substance inside the liquid, this procedure is sufficient for determining the concentration in the liquid.

Advantageously, the device has at least one beam splitter for splitting the light emitted by the laser into at least two partial beams, which are conducted through the flow-through chamber along the at least two paths. As a result, the different paths which the light must pass through inside the flow-through chamber can be realized without the light being reflected at the peripheral wall of the flow-through chamber or at some other reflector element. This may be useful for certain requirements, since, for example, no reflecting surface thereby comes into contact with the liquid and the chemical substance dissolved therein. Naturally, it is possible to combine both principles together, and so, in a beam-splitting device, the light emitted by the laser is split into multiple partial beams, of which at least one or all, preferably all except for one, are subsequently reflected inside the flow-through chamber and each separately passes through the flow-through chamber along multiple different paths. After the individual partial beams have left the flow-through chamber, they are, for example, brought together and jointly conducted onto the detector, which measures the total intensity of the light. Naturally, it is also possible for the individual partial beams to be fed separately to a detector and for the individual intensity results determined in this way to be combined to give an overall result.

Advantageously, at least one of the partial beams is not conducted through the flow-through chamber. Said beam serves as the reference beam and is advantageously directly conducted either onto a detector separately intended therefor or onto the detector present in any case. This means that the incident laser light intensity as reference value can be measured and simultaneously monitored. This makes it possible to prevent malfunctions of the device. If the detector detects, for example, a strong decrease in the intensity of the laser light arriving thereat, this can mean, on the one hand, an especially high concentration of the chemical substance dissolved in the liquid and thus a large absorption of the laser light in the liquid. However, this detection result can, for example, also be caused by a decrease in the incident laser light intensity, for example as a result of a malfunction or a laser aging process. Said result can be determined by a separate partial beam which is not guided through the flow-through chamber, and so incorrect interpretations of the measurement results are prevented here.

In a particularly preferred design, the device has at least two lasers for emitting light of the absorption wavelength. With this design too, it is possible to particularly easily achieve the light of the lasers being conducted through the flow-through chamber on two different paths, by the light of the two lasers being separately conducted into the flow-through chamber through an entry window and conducted out of the flow-through chamber through an exit window. This too can be naturally combined with the principles already described. Thus, the light emitted by both lasers can, for example, also be split by a beam splitter and/or reflected by means of mirrors inside the flow-through chamber, and so the path length covered by the laser light inside the flow-through chamber is likewise freely adjustable here. In this way too, it is possible, for example, to distinguish aging effects or malfunctions of one of the two lasers from an increased concentration of the chemical substance to be detected in the liquid, by, for example, separately measuring the intensity of the laser light striking the detector for both lasers and thus making a comparison.

It has been found to be particularly advantageous when one of the partial beams, which is for example emitted by one of the two lasers, is guided through the flow-through chamber, but does not come into contact therein with the liquid and the chemical substance dissolved therein. This can, for example, be effected by means of a channel or a waveguide. In this way, it is possible to ensure that, for example, shadowing effects of the entry and/or exit window cannot be confused with an elevated concentration of the chemical substance to be detected. If the detector detects a strong decrease in the laser light intensity arriving thereat, this can be due not only to the elevated concentration of the chemical substance to be detected, but also to a shadowing or clouding of the entry and/or exit window through which the laser light is conducted into the flow-through chamber or conducted out of the flow-through chamber. This can be differentiated by means of a separate partial beam which is guided through the entry and exit windows, but does not come into contact with the liquid and the substance dissolved therein.

Advantageously, the two lasers emit light of differing wavelength. This means that it is possible to increase the number of the distinguishable dissolved chemical substances. To be able to unequivocally identify the dissolved chemical substance using the presently described device, it is necessary that the chemical substance absorbs light of the absorption wavelength and no other possible chemical substance does this too. Only in this case is it possible to unambiguously identify the chemical substance to be detected. However, if there are, for example, multiple, for example three or four, chemical substances which absorb light of the absorption wavelength, it is extremely unlikely that some or all of said substances also absorb light at a second absorption wavelength different from the first absorption wavelength. If the second laser is then adjusted to this wavelength, it is possible to separate the chemical substances which are not distinguishable by only one absorption line.

As already described, it is advantageous when the second laser emits light of a second wavelength, which light is not absorbed by the chemical substance to be detected. In this way, said light can be used for determining scattering and absorption mechanisms which are not dependent on the chemical substance which is to be detected. In this connection, it has been found to be particularly advantageous when the light of the two lasers is conducted through the flow-through chamber along the same path or along paths of equal length before it hits the detector. In this way, it is ensured that the scattering and absorption mechanisms and processes occurring due to contaminants and other disturbances influence the light of both lasers to the same extent. If the light of the two lasers is conducted through the flow-through chamber along the same path, inhomogeneities in the distribution of the impurities, for example the distribution of bubbles or suspended particles in the liquid, can also be taken into account and no longer contribute to a falsification of the measurement result. The detector, which has to detect the light of two different lasers having differing wavelength, can also be designed in the form of two separate detector elements, which are possibly arranged at different positions. Naturally, it is also possible to use one detector which is capable of simultaneously detecting the light of different wavelengths and determining the respective intensities. This is also the case when multiple lasers emitting light of different absorption wavelengths are used.

Preferably, the flow-through chamber has at least one window, through which the light emitted by the laser can penetrate into the flow-through chamber and leave the flow-through chamber, the at least one window preferably consisting of a glass. The window can, for example, be attached to the peripheral wall of the flow-through chamber by means of a coating or by means of an adhesive. Naturally, it is also possible for multiple windows, more particularly an entry window and an exit window, to be present, and so the light emitted by the laser can enter the flow-through chamber and exit therefrom at different positions.

A method according to the invention for producing a flow-through chamber for a presently described device is notable for the following steps:
a) producing an indentation in a workpiece,
b) positioning at least one peripheral wall element in the indentation, the peripheral wall element being a substrate produced in a coating method and mirror-covered at least in one reflection segment,
c) closing the indentation with a lid element.

This is only one way of producing a flow-through chamber for a presently described device. In this case, the peripheral wall element is produced especially as a substrate which, outside the indentation of the workpiece, is provided with a mirror coating which, for example, can be applied in a thin film method. Subsequently, the peripheral wall element is positioned in the indentation of the workpiece. Said indentation can, for example, be removed from the workpiece by milling or etching and is advantageously somewhat larger, in terms of its spatial extent, than the subsequent flow-through chamber. The peripheral wall element, which is arranged in the indentation, forms at least one portion of the peripheral wall and has the reflection segment required for reflecting the laser light directed by the laser.

By means of the method according to the invention, it is possible to first produce the indentation, it being possible for the manufacturing tolerances to be observed to be relatively generously dimensioned, since the peripheral wall elements, which must be exactly orientated to one another, are inserted later. Therefore, the indentation can be produced rapidly and cost-effectively. Separately to this, the substrate is mirror-coated in the region of the reflection segment and then inserted into the indentation in the form of the peripheral wall element. In this case, it can be brought exactly into the desired position and orientation. Subsequently, the indentation is closed with a lid element, which forms a further portion of the peripheral wall. This means that the flow-through opening is closed to the extent that only an inlet and an outlet opening are present. The peripheral wall element can moreover comprise an entry and/or exit window, which, for example, is attached to the substrate as a separate glass component. To this end, all established methods known from the prior art can be used.

It has been found to be particularly advantageous when two peripheral wall elements are positioned opposite one another in the indentation. The orientation of said two elements, which each advantageously comprise at least one reflection segment, can be effected exactly in the desired and required position. The production of such a flow-through chamber is therefore possible in a rapid, simple and thus cost-effective manner.

The provided peripheral wall element and, in particular, reflection segment is, for example, a lapped aluminum reflection element sputtered with silicon dioxide. To this end, an aluminum block can be coated, more particularly sputtered, with thin silicon dioxide in order to avoid a refraction of the light beam. A lid element is then adhesively bonded, for example using silicone, onto the indentation in which the peripheral wall element is situated.

In a particularly preferred variant, it is possible to produce a bottom base plate of the flow-through chamber, for example composed of a glass, onto which the silicon dioxide-sputtered aluminum blocks and the optional entry and/or exit window are adhesively bonded. It is possible to bond thereto the inlet opening and/or the outlet opening for the liquid, for example using silicone. Subsequently, the lid is fitted and the entire construction is sealed, for example using silicone.

Alternatively, a coating of manganese(II) fluoride is also conceivable. However, both are only exemplary designs which can be replaced by more suitable combinations depending on the liquid used and dissolved chemical substance to be detected.

In an alternative method for producing the flow-through chamber for a presently described device be taken off from a master or master component, which, for example, can be produced by machining of a material block. Said block can, for example, be surrounded by a mold material, for example silicone, by casting, which material is removed from the master or master component after hardening and thus forms the mold. Naturally, other ways of producing an appropriate mold are also conceivable. After providing the mold, casting is carried out by filling said mold with a chamber material. In this case, the chamber material is the material from which the flow-through chamber to be produced is to be produced. The chamber material hardens in the mold. This can be effected by cooling, and so, if applicable, it is merely necessary to wait until the possibly warm or hot chamber material cools down. Naturally, it is also possible to use a cooling system and to allow the chamber material to cool down using a defined temperature profile as a function of time and to thus favor or ensure, for example, certain crystal structures or other solidification forms.

After hardening of the chamber material, the thus hardened material is removed from the mold. In this connection, the mold and the material are selected such that the removed hardened chamber material forms at least one portion of the flow-through chamber. This portion includes especially at least one portion of the peripheral wall, which portion comprises the at least one reflection segment. In this way, it is possible, in an easy-to-perform and easy-to-control method, to optimally arrange the reflection segments relative to one another and to an inlet and outlet opening possibly yet to be produced at a later time. Naturally, inlet opening and/or outlet opening can also be already provided by an appropriate shape of the mold, and so they are already created by the casting process. The reflection segments can thus preferably be created with a surface roughness smaller than the wavelength of the light to be reflected at the reflection segments. Owing to the fact that they are designed as one piece with the main portion of the flow-through chamber or the entire flow-through chamber, a positioning of the individual reflection segments is possible without any problems.

A comparatively cost-intensive and error-prone sticking-in and orientation of the mirrors is thus no longer necessary.

Advantageously, the device has a temperature-adjustment unit which can increase and/or decrease the temperature of the liquid situated in the flow-through chamber in order to ensure a constant temperature within the flow-through chamber. In a preferred design, the reflection segments can be used as heating elements. In the flow-through direction upstream of the flow-through chamber, there is advantageously at least one temperature sensor which determines the temperature of the liquid medium. The thus determined value can be used for controlling the temperature-adjustment unit and for increasing or decreasing the temperature of the liquid if necessary.

In an advantageous design, a reference measurement is moreover possible. The light emitted by the two lasers is conducted through a second flow-through chamber which is advantageously designed identically to the flow-through chamber of the device. However, said second flow-through chamber is subjected to flow-through by a liquid in which the concentration of the chemical substance to be detected is known. In this way, it is possible to carry out a reference measurement and thus further improve the quality of the actual measurement.

Figure 2:
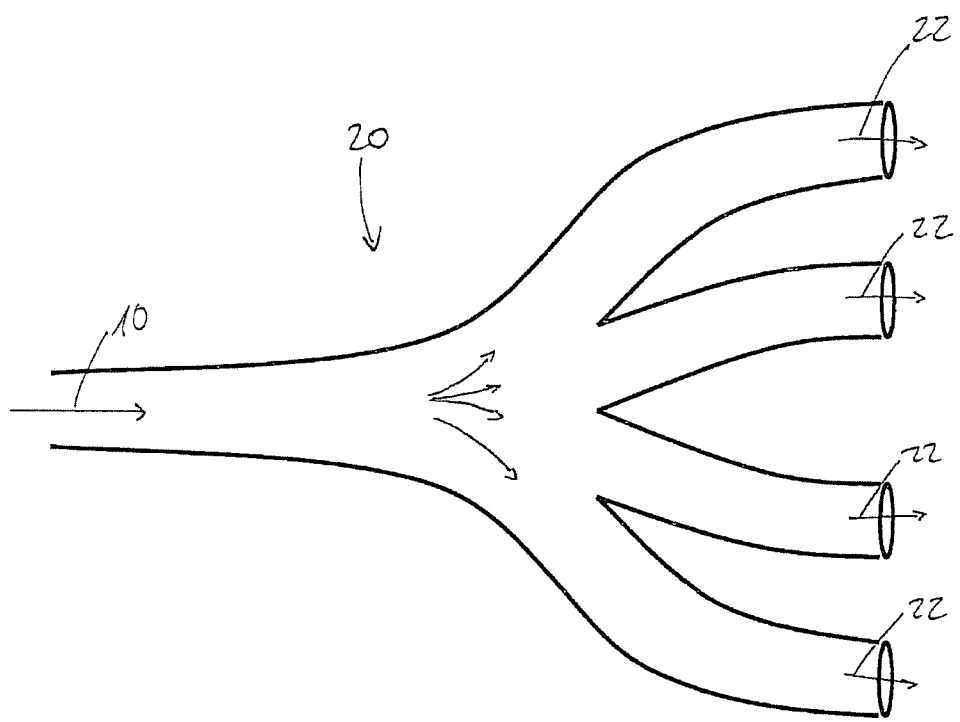
Figure 3:
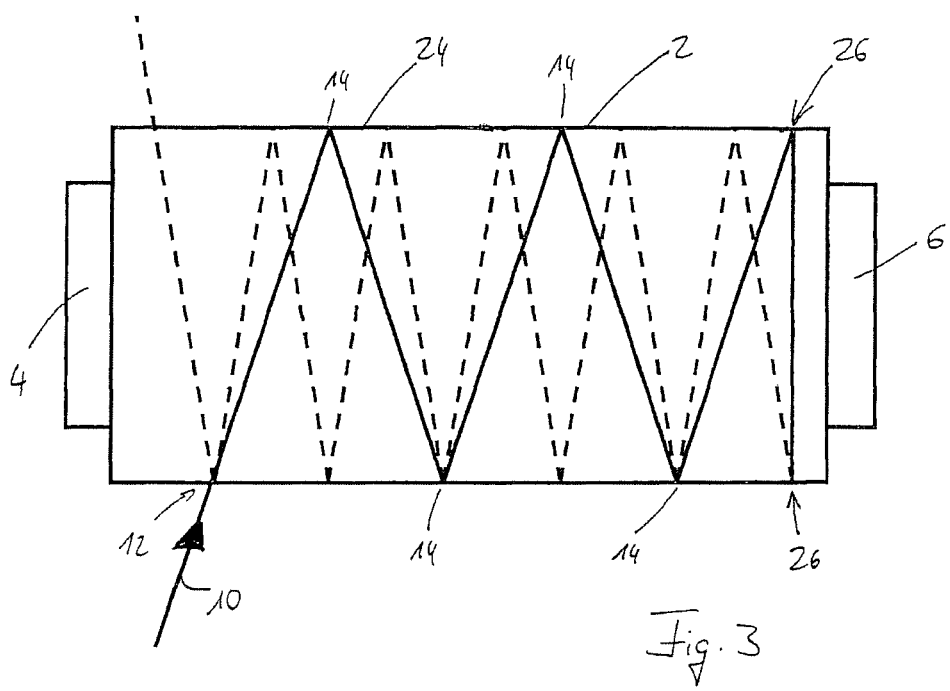
Figure 4:
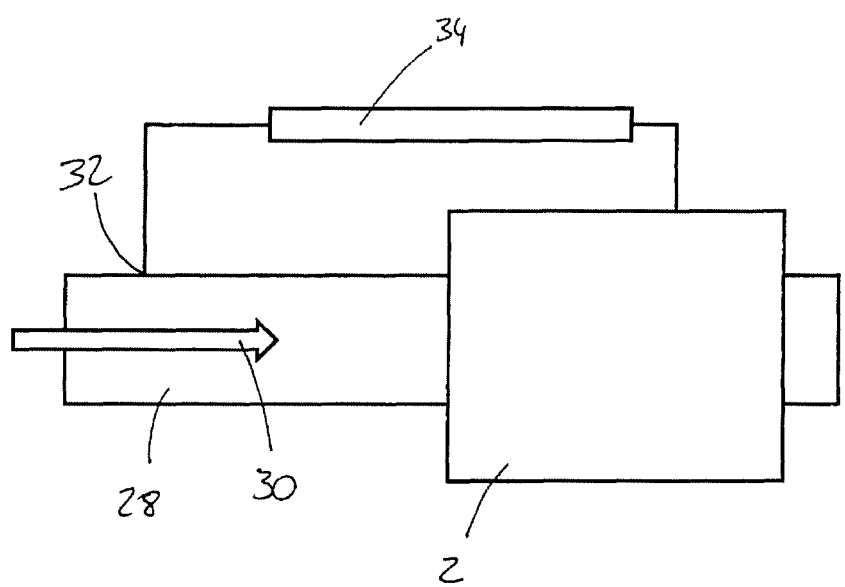

An exemplary embodiment of the present invention will be more particularly elucidated below with the aid of the attached figures, showing:

FIG. 1—the schematic top view of a device according to a first exemplary embodiment of the present invention FIG. 2—the schematic view of a beam splitter FIG. 3—the schematic top view of a flow-through chamber of a device according to a further exemplary embodiment of the present invention and FIG. 4—the schematic representation of a device according to a further exemplary embodiment of the present invention.

FIG. 1 shows a device according to a first exemplary embodiment of the present invention. Said device has a flow-through chamber 2 which comprises an inlet opening 4 and an outlet opening 6, the inlet opening 4 and the outlet opening 6 being designed in the form of a flange in the exemplary embodiment shown in FIG. 1. Consequently, a liquid flows through the flow-through chamber 2 from left to right in the exemplary embodiment shown in FIG. 1.

The device has moreover a laser 8 which emits light 10 having a wavelength corresponding to the absorption wavelength of the dissolved chemical substance. The light 10 enters the flow-through chamber 2 through an entry window 12 and is reflected at three reflection segments 14 intended therefor. Subsequently, said light exits the flow-through chamber 2 through an exit window and falls onto a detector 18, which measures the intensity of the incident light 10. From the loss in intensity of the light 10 from the laser 8 up to the detector 18, it is possible to determine the concentration of a chemical substance dissolved in the liquid. Since the light 10 is reflected three times at the reflection segments 14 inside the flow-through chamber 2 in the exemplary embodiment shown, the distance covered by the light 10 inside the flow-through chamber 2 is distinctly greater than a spatial extent of the flow-through chamber 2. It is thus possible for the flow-through chamber 2 and thus the entire device to be designed to be spatially small.

The flow-through chamber 2 has a longitudinal extent in the longitudinal direction L, corresponding to the direction of flow of the liquid from the inlet opening 4 to the outlet opening 6 in the exemplary embodiment shown. Via a selection of the angle which the light 10 occupies inside the flow-through chamber 2 having said longitudinal direction L, it is also possible to adjust the number of the reflections at the reflection segments 14. If the angle between the incident light 10 and the longitudinal direction L is increased, said angle will thus approach 90°, the light 10 can be reflected at a larger number of reflection segments 14 to be arranged though therefor, and so the distance covered by the light 10 inside the flow-through chamber increases. This means that the sensitivity of the device 1 is increased.

As an alternative or in addition to the device shown in FIG. 1, the light 10 emitted by the laser 8 can be transmitted by means of a beam splitter 20, as depicted in FIG. 2. The light 10 enters the beam splitter 20 from the left and is split into four partial beams 22. Naturally, beam splitters 20 which generate more than four or less than four partial beams 22 are also conceivable. The partial beams 22 can, analogously to the exemplary embodiment shown in FIG. 1, be conducted into the flow-through chamber 2 through an entry window 12 and be reflected therein at, for example, reflection segments 14 intended therefor. Arranged between the exit window 16 and the detector 8 is a further beam splitter 20, which, however, has the light passing through in the reverse direction, and so the different impinging partial beams 22 are bundled to form one light beam and then detected by the detector 18. As an alternative to this, it is naturally also possible to separately detect the individual partial beams 22 on the detector 18, the result subsequently being added up to give an overall result.

Especially when multiple partial beams 22 are introduced into the flow-through chamber 2, it is frequently not necessary to use separate reflection segments 14 in order to reflect the partial beams 22 inside the flow-through chamber 2. On the contrary, the partial beams 22, after they have passed once through the flow-through chamber 2, can leave the flow-through chamber 2 through the exit window 16. Each of the partial beams 22 then forms one of the different paths. In this case too, the path length covered by the light inside the flow-through chamber 2 is increased. As a result, the light 10 has the chance of hitting more molecules of the chemical substance to be detected in the liquid and of thus yielding a detectable signal, i.e., a measurable intensity reduction. As a result, it is possible to detect even relatively small and most minute concentrations of the chemical substance.

FIG. 3 shows a schematic representation of a further device. The flow-through chamber 2 having inlet opening 4 and outlet opening 6 can be identified. The light 10, which penetrates into the flow-through chamber 2 through the entry window 12, which is integrated into a peripheral wall 24 of the flow-through chamber 2 in the exemplary embodiment shown in FIG. 3, is reflected by the peripheral wall 24. In the exemplary embodiment shown in FIG. 3, the entire peripheral wall 24 is advantageously mirror-coated on the inside. Whereas the light 10 is still situated in the same plane as the entry light 10 after the first four reflection segments 14, said light is deflected at deflection points 26 into a second plane, which is below the first plane in the exemplary embodiment shown in FIG. 3. In this area, the light 10 is depicted by a dashed line, whereby the intention is merely to show that the light 10 now proceeds in a displaced manner in a direction perpendicular to the drawing plane. It can be seen that the reflection angles in this plane are smaller, and so a different number of crossings must be undertaken by the light 10.

FIG. 3 merely serves as an example of the virtually unlimited diversity of possible beam paths inside the flow-through chamber 2. Both the inclination relative to the longitudinal direction L and the number of the different planes or other beam guidance of the light 10 inside the flow-through chamber 2 is determined in particular by the required path length covered by the light 10 inside the flow-through chamber 20. Said path length should be adapted to the expected concentration of the chemical substance to be detected.

FIG. 4 shows schematically a flow-through chamber 2 having a feed line 28. Said feed line is subjected to flow-through of liquid along the arrow 30, which liquid penetrates into the flow-through chamber 2 through an inlet opening that is not shown. Situated on the feed line 28 is a temperature sensor 32 which makes it possible to determine the temperature of the liquid in the feed line 28. The thus determined value is fed to an electronic control system 34 which is connected to heating and/or cooling elements that are not shown, therefore to a temperature-adjustment unit inside the flow-through chamber 2. In this way, it is possible to ensure a constant temperature in the flow-through chamber 2.

LIST OF REFERENCE SIGNS

L Longitudinal direction
2 Flow-through chamber
4 Inlet opening
6 Outlet opening
8 Laser
10 Light
12 Entry window
14 Reflection segment
16 Exit window
18 Detector
20 Beam splitter
22 Partial beam
24 Peripheral wall
26 Deflection point
28 Feed line
30 Arrow
32 Temperature sensor
34 Electronic control system

The invention claimed is:

1. A device for determining a concentration of a chemical substance dissolved in a liquid, which substance absorbs light of at least one absorption wavelength, comprising:
   at least one flow-through chamber having
      at least one inlet opening,
      at least one outlet opening, and
      at least one peripheral wall;
   at least two lasers which emit light of differing wavelengths, wherein said at least two lasers include at least one laser for emitting light of the at least one absorption wavelength; and
   at least one detector for detecting emitted light,
   wherein at least one of the at least one peripheral wall has at least one reflection segment which is arranged such that emitted light from at least some of the at least two lasers is deflected at the reflection segment from a first path to a second path, the different paths being in different planes.

2. The device as claimed in claim 1, wherein emitted light from at least some of the at least two lasers is reflected multiple times by the at least one reflection segment of the at least one peripheral wall before it is detected by the detector.

3. The device as claimed in claim 1, further comprising at least one beam splitter for splitting emitted light from at least some of the at least two lasers into at least two partial beams, of which at least one of said at least two partial beams is conducted through the at least one flow-through chamber along at least two paths.

4. The device as claimed in claim 3, wherein at least a second of the at least two partial beams is not conducted through the at least one flow-through chamber.

5. The device as claimed in claim 1, wherein the at least two lasers includes at least a second laser which emits light of a second wavelength, which light is not absorbed by the chemical substance at the at least one absorption wavelength.

6. The device as claimed in claim 5, wherein emitted light of both the at least one laser and the at least a second laser is conducted through the at least one flow-through chamber along a same path or along paths of equal length before detection by the detector.

7. The device as claimed in claim 1 wherein the at least one flow-through chamber has at least one window through which emitted light from at least some of the at least two lasers can penetrate into the at least one flow-through chamber and leave the at least one flow-through chamber.

8. A method for producing a flow-through chamber having at least one inlet opening, at least one outlet opening, and at least one peripheral wall, the method comprising the following steps:
   a) producing an indentation in a workpiece,
   b) positioning at least one peripheral wall element in the indentation, the peripheral wall element being a substrate produced in a coating method and mirror-covered at least in one reflection segment, wherein at least one of the at least one reflection segment is arranged such that emitted light is deflected at the reflection segment from a first path to a second path, the different paths being in different planes, and
   c) closing the indentation with a lid element.

9. The method as claimed in claim 8, wherein the at least one peripheral wall element includes two peripheral wall elements, and wherein the two peripheral wall elements are positioned opposite one another in the indentation.

10. A method for producing a flow-through chamber having at least one inlet opening, at least one outlet opening, and at least one peripheral wall, the method comprising the steps of:
   a) providing a mold,
   b) carrying out casting by filling the mold with a chamber material,
   c) hardening the chamber material in the mold, and
   d) removing the hardened chamber material from the mold, the mold and the chamber material being such that the hardened chamber material forms a flow-through chamber having at least one portion of the peripheral wall and at least one reflection segment, wherein at least one of the at least one reflection segment is arranged such that emitted light is deflected at the reflection segment from a first path to a second path, the different paths being in different planes.

11. The device as claimed in claim 7 wherein the at least one window is made of glass.

* * * * *